(12) United States Patent
Erickson et al.

(10) Patent No.: US 8,691,797 B2
(45) Date of Patent: Apr. 8, 2014

(54) CHLORINATION OF CARBOHYDRATES AND CARBOHYDRATE DERIVATIVES

(71) Applicant: Lexington Pharmaceuticals Laboratories, LLC, Carmel, IN (US)

(72) Inventors: William Randal Erickson, Carmel, IN (US); Stephen Craig Fields, Fishers, IN (US)

(73) Assignee: Lexington Pharmaceuticals Laboratories, LLC, Carmel, IN (US)

( * ) Notice: Subject to any disclaimer, the term of this patent is extended or adjusted under 35 U.S.C. 154(b) by 0 days.

(21) Appl. No.: 13/826,851

(22) Filed: Mar. 14, 2013

(65) Prior Publication Data

US 2013/0197215 A1    Aug. 1, 2013

Related U.S. Application Data

(63) Continuation of application No. PCT/US2012/060068, filed on Oct. 12, 2012.

(60) Provisional application No. 61/547,356, filed on Oct. 14, 2011.

(51) Int. Cl.
*C07H 1/00* (2006.01)

(52) U.S. Cl.
USPC .................. 514/124; 536/4.1; 536/123.13

(58) Field of Classification Search
USPC ...................... 536/4.1, 123.13, 124
See application file for complete search history.

(56) References Cited

U.S. PATENT DOCUMENTS

| | | | |
|---|---|---|---|
| 4,380,476 A | 4/1983 | Mufti et al. | |
| 4,435,440 A | 3/1984 | Hough et al. | |
| 4,634,784 A | 1/1987 | Nagato et al. | |
| 4,762,537 A | 8/1988 | Fleming et al. | |
| 4,980,463 A | 12/1990 | Walkup et al. | |
| 5,254,153 A | 10/1993 | Mudder | |
| 5,498,709 A | 3/1996 | Navia et al. | |
| 6,206,950 B1 | 3/2001 | Ireland | |
| 6,368,568 B1 | 4/2002 | Lord | |
| 6,503,396 B2 | 1/2003 | Kim et al. | |
| 6,831,181 B2 | 12/2004 | Bhatia | |
| 6,860,985 B2 | 3/2005 | Siskin et al. | |
| 6,936,724 B2 | 8/2005 | Ohara et al. | |
| 7,262,327 B2 | 8/2007 | Mendelovici et al. | |
| 7,425,258 B2 | 9/2008 | Chen et al. | |
| 7,626,016 B2 | 12/2009 | Wu et al. | |
| 7,741,477 B2 * | 6/2010 | Deshpande et al. | 536/124 |
| 7,910,727 B2 | 3/2011 | Li et al. | |
| 8,153,849 B2 | 4/2012 | Scherrer et al. | |
| 2004/0030124 A1 | 2/2004 | Catani et al. | |
| 2004/0260039 A1 | 12/2004 | Yoshimura et al. | |
| 2005/0191396 A1 | 9/2005 | Seltzer et al. | |
| 2007/0100139 A1 | 5/2007 | Fry | |
| 2007/0207246 A1 | 9/2007 | Wang et al. | |
| 2008/0103295 A1 | 5/2008 | Ho et al. | |
| 2008/0125584 A1 | 5/2008 | Ratnam et al. | |
| 2008/0163867 A1 | 7/2008 | Subramanyam et al. | |
| 2008/0227971 A1 | 9/2008 | Leinhos et al. | |
| 2008/0234526 A1 | 9/2008 | Scherrer et al. | |
| 2008/0300391 A1 | 12/2008 | Ratnam et al. | |
| 2008/0300392 A1 | 12/2008 | Xu | |
| 2008/0300401 A1 | 12/2008 | Xu | |
| 2009/0105470 A1 | 4/2009 | Ratnam et al. | |
| 2009/0118493 A1 | 5/2009 | Ratnam et al. | |
| 2009/0131653 A1 | 5/2009 | Ratnam et al. | |
| 2009/0163704 A1 | 6/2009 | Ratnam et al. | |
| 2009/0208747 A1 | 8/2009 | Ratnam et al. | |
| 2009/0259034 A1 | 10/2009 | Kerr et al. | |
| 2009/0259036 A1 | 10/2009 | Wiley, Jr. | |
| 2009/0264640 A1 | 10/2009 | Ratnam et al. | |
| 2009/0281295 A1 | 11/2009 | Micinski et al. | |
| 2009/0299055 A1 | 12/2009 | Wiley, Jr. et al. | |
| 2009/0324513 A1 | 12/2009 | Ratnam et al. | |
| 2010/0022765 A1 | 1/2010 | Ho et al. | |
| 2010/0056773 A1 | 3/2010 | Chandrasekhar et al. | |
| 2010/0081803 A1 | 4/2010 | Micinski et al. | |

(Continued)

FOREIGN PATENT DOCUMENTS

| | | |
|---|---|---|
| EP | 1923379 A1 | 5/2008 |
| WO | WO 2007/054971 A2 | 5/2007 |

(Continued)

OTHER PUBLICATIONS

European Patent Office, International Search Report and Written Opinion issued in parent PCT International Application No. PCT/US2011/061796 on Feb. 7, 2012.

(Continued)

*Primary Examiner* — Elli Peselev
(74) *Attorney, Agent, or Firm* — Leydig, Voit & Mayer, Ltd.

(57) ABSTRACT

Disclosed is a method for chlorinating a carbohydrate or a derivative thereof to produce a polychlorinated carbohydrate or a derivative thereof, such as sucralose, the method involves (i) reacting the carbohydrate or derivative thereof with a chlorinating agent to obtain a reaction mixture comprising said polychlorinated carbohydrate or derivative thereof and at least one under-chlorinated carbohydrate or derivative thereof, (ii) returning the at least one under-chlorinated carbohydrate or derivative thereof to a chlorinating step and further chlorinating the at least one under-chlorinated carbohydrate or derivative thereof to obtain the desired polychlorinated carbohydrate or derivative thereof; and (iii) optionally repeating steps (i) and (ii) "n" times where $n \geq 1$. The polychlorinated carbohydrate or a derivative thereof is obtained in high yields.

24 Claims, No Drawings

(56) References Cited

U.S. PATENT DOCUMENTS

| | | |
|---|---|---|
| 2010/0160625 A1 | 6/2010 | Ratnam et al. |
| 2010/0168412 A1 | 7/2010 | Ratnam et al. |
| 2010/0184969 A1 | 7/2010 | Rajadhyaksha et al. |
| 2010/0202570 A1 | 8/2010 | Tsai et al. |
| 2010/0216195 A1 | 8/2010 | Ratnam et al. |
| 2010/0228020 A1 | 9/2010 | Ratnam et al. |
| 2010/0292462 A1 | 11/2010 | Chen et al. |

FOREIGN PATENT DOCUMENTS

| | | |
|---|---|---|
| WO | WO 2007/099557 A2 | 9/2007 |
| WO | WO 2008/052076 A2 | 5/2008 |
| WO | WO 2008/096928 A1 | 8/2008 |
| WO | WO 2010/109189 A1 | 9/2010 |
| WO | WO 2010/151489 A1 | 12/2010 |
| WO | WO 2012/071385 A1 | 5/2012 |
| WO | WO 2013/056128 A1 | 4/2013 |

OTHER PUBLICATIONS

European Patent Office, International Search Report and Written Opinion issued in related PCT International Application No. PCT/US2012/060068 on Dec. 18, 2012.

Kresge, Charles T. et al., "Molecular Sieves," *Kirk-Othmer Encyclopedia of Chemical Technology*, vol. 16, John Wiley and Sons, Incorporated, pp. 811-853, pub. Date Oct. 2005 © 2006.

Scherrer, Stephen C. et al. inventors, partial file history of U.S. Appl. No. 11/999,381 (now US 8,153,849) from filed of Dec. 4, 2007 through filing of Response to Final Office Action filed Jul. 11, 2011; 391 pages.

Copp, James D. et al., "Optimization of the penicillin ring expansion reaction through the use of an alkene as an HCl scavenger," *Organic Process Research & Development*, 1997, 1: 92-94.

United States Patent and Trademark Office. Office Action issued in related U.S. Appl. No. 13/826,493 on Jun. 20, 2013.

\* cited by examiner

CHLORINATION OF CARBOHYDRATES AND CARBOHYDRATE DERIVATIVES

CROSS-REFERENCE TO A RELATED APPLICATION

This application is a continuation of International Patent Application No. PCT/US2012/060068, filed Oct. 12, 2012, claiming the benefit of U.S. Provisional Patent Application No. 61/547,356, filed Oct. 14, 2011, the disclosures of which are incorporated herein by reference.

BACKGROUND OF THE INVENTION

Chlorination of carbohydrates and derivatives thereof, such as sugars and their esters, has been generally known. For example, chlorination of sucrose to produce sucralose, or 4,1',6'-trichloro-4,1',6'-trideoxygalactosucrose, which is an artificial sweetener with a sweetness intensity many times that of sucrose, has been disclosed in U.S. Pat. No. 4,980,463; WO 2008/052076 A2, U.S. 2007/0100139 A1, and U.S. 2007/0207246 A1. Sucralose can be made by chlorination of a sucrose ester such as sucrose-6-acetate or sucrose-6-benzoate. However, the yields reported in the art for sucralose-6-ester are generally low. For example, the '463 patent discloses examples of preparing sucralose-6-benzoate in molar yields ranging from 31.9% to 60%. WO '076 discloses examples of preparing sucralose-6-acetate in a molar yield of 62.5%.

The foregoing shows that there exists an unmet need for preparing polychlorinated carbohydrates or derivatives thereof, particularly sucralose-6-ester in high molar yields.

BRIEF SUMMARY OF THE INVENTION

The invention provides a method for chlorinating a carbohydrate or a derivative thereof to produce a polychlorinated carbohydrate or a derivative thereof in high yields. The method involves recovering and returning at least a portion of the under-chlorinated carbohydrate or a derivative thereof to a chlorinating step so as to further chlorinate the under-chlorinated carbohydrate or a derivative thereof to the desired polychlorinated carbohydrate or a derivative thereof. These recovering and returning steps can be repeated any desired number of times, thereby obtaining high yields of the polychlorinated carbohydrate or derivative thereof, particularly sucralose-6-esters.

The present invention therefore offers one or more of the following advantages: increased yield of the desired polychlorinated carbohydrate esters, reduced waste stream and/or disposal of the partially or under-chlorinated carbohydrate esters, potential reduced energy demands, reduced demand for raw materials, and/or improved process economy. The present invention thus provides also an economic advantage over processes known in the art.

DETAILED DESCRIPTION OF THE INVENTION

Accordingly, the invention provides a method for chlorinating a carbohydrate or a derivative thereof to produce a polychlorinated carbohydrate or a derivative thereof, said polychlorinated carbohydrate or a derivative thereof having a desired number of chlorine atoms in desired locations in its molecular structure, the method comprising:

(i) reacting the carbohydrate or derivative thereof with a chlorinating agent to obtain a reaction mixture comprising said polychlorinated carbohydrate or derivative thereof and at least one under-chlorinated carbohydrate or derivative thereof;

(ii) returning the at least one under-chlorinated carbohydrate or derivative thereof to a chlorinating step and further chlorinating the at least one under-chlorinated carbohydrate or derivative thereof to obtain the desired polychlorinated carbohydrate or derivative thereof; and (iii) optionally repeating steps (i) and (ii) "n" times where $n \geq 1$.

In accordance with the invention, any suitable carbohydrate or derivative thereof, which has at least two, three, four, five, or more hydroxyl groups may undergo chlorination. In an embodiment, the carbohydrate or a derivative thereof has at least three hydroxyl groups that are chlorinated by the method of the present invention.

The carbohydrate can be a monosaccharide, oligosaccharide, or polysaccharide. The oligosaccharide can be disaccharide, trisaccharide, tetrasaccharide, or a higher saccharide. An example of a disaccharide is sucrose. Examples of higher saccharides include starches, cellulose, hemicelluloses, gums, dextrans, gellan, pullulan, scleroglucan, welan, xanthans, agars, algins, carrageenans, furcellarans, pectins, chitins, and chitosans.

In an embodiment, the carbohydrate derivative can also be a nucleoside, e.g., uridine, deoxyuridine, adenosine, deoxyadenosine, guanosine, deoxyguanosine, thymidine, deoxythymidine, cytidine, deoxycytidine, or a nucleotide such as DNA or RNA. In accordance with the invention, the carbohydrate derivative can be one where a carbohydrate molecule is covalently linked to another molecule, e.g., any other polymer molecule.

In accordance with an embodiment of the invention, the carbohydrate or derivative thereof is a sugar or derivative thereof. Examples of suitable sugars include sucrose, maltose, lactose, erythrose, threose, ribose, arabinose, xylose, lyxose, allose, altrose, glucose, mannose, gulose, idose, galactose, and talose, particularly sucrose.

In an embodiment, the carbohydrate or sugar derivative is an ester. In a particular embodiment, the sugar the sugar derivative is a sugar ester, more particularly a sucrose ester.

In accordance with the inventive method, the polychlorinated carbohydrate or a derivative thereof can retain the stereochemical configuration of one or more groups on the carbohydrate ring structure or the stereochemical configuration of one or more groups on the carbohydrate ring structure of the polychlorinated carbohydrate or a derivative thereof could be different than that of the starting carbohydrate or a derivative thereof.

In accordance with an embodiment of the inventive method, the polychlorinated carbohydrate ester or the under-chlorinated ester is of the formula: M-OC(=O)R', wherein R' comprises a hydrophobic group or a hydrophobic polymer and M is the moiety completing the rest of the polychlorinated carbohydrate ester or the under-chlorinated ester. For example, R' comprises a hydrophobic group or a hydrophobic polymer such that the polychlorinated carbohydrate ester or the under-chlorinated ester has an octanol-water partition coefficient (Kow) of LogP or calculated (cLogP) of −0.5 or greater. The LogP or cLogP value describes a compound's propensity to distribute itself between octanol and water: a measurement of how lipophilic and/or hydrophobic it is. When compounds either are not known or are known but their LogP values have not been physically measured, methods of calculating cLogP values are available.

There are several professional programs that can make the above described calculations which are readily accessible: for example, SciFinder™ offers one—Advanced Chemistry Development (ACD/Labs) Software V11.02. There are also freeware resources such as that offered by ChemAxon™.

In an embodiment of the invention, the polychlorinated carbohydrate ester or the under-chlorinated carbohydrate ester has an octanol-water partition coefficient LogP or cLogP of 0 or greater than 0, for example, from 0.05 to about 5, and in an embodiment from about 0.5 to about 3. For example, monochlorosucrose-6-benzoate ester has a cLogP of 0.7; dichlorogalactosucrose-6-benzoate has a cLogP of 1.5 (interpolated value); 4,1',6'-trichloro-4,1',6'-trideoxy-6-O-benzoate ester of galactosucrose (TGS6B) has a cLogP of 2.6. 4,1',6'-trichloro-4,1',6'-trideoxy-6-O-acetate ester of galactosucrose (TGS6A) has a cLogP of 0.18, dichlorogalactosucrose-6-acetate ester has a cLogP of 0.06, and monochlorosucrose-6-acetate ester has a cLogP of −0.85.

In accordance with an embodiment of the inventive method, R is alkyl, aryl, or arylalkyl, wherein the aryl part of aryl or arylalkyl is optionally substituted with one or more substituents selected from the group consisting of halo, haloalkyl, cyano, nitro, alkoxy, alkylthio, acyl, acyloxy, thioacyl, acylthio, and aryloxy. In a particular embodiment, R' is aryl, e.g., phenyl, each of which is optionally substituted with one or more substituents selected from the group consisting of halo, haloalkyl, cyano, nitro, alkoxy, alkylthio, acyl, acyloxy, thioacyl, acylthio, and aryloxy. In certain embodiments, R' comprises a hydrophobic polymer. For example, R' could include a hydrophobic or hydrophilic group but in addition a polymer with the net result that R' is hydrophobic.

Any suitable ester stable to the chlorinating agent, and which can be hydrolyzed can be used in the present invention. The ester can be a $C_1$-$C_{18}$ aliphatic, $C_6$-$C_{14}$ aryl $C_1$-$C_{18}$ aliphatic or $C_6$-$C_{14}$ aryl ester. Particularly suitable carboxylate esters include $C_6$-$C_{10}$ aryl carboxylates such as benzoate or naphthoate ester. The ester can be prepared by acylation of the carbohydrate or sugar using an acylating agent of the relevant acid, and in the case of carboxylic acylation, it is an acyl anhydride or acyl halide. Alternatively, the carbohydrate can be esterified by enyl esters.

In an embodiment of the inventive method, the sugar ester is a sucrose-6-ester and the chlorinated product is chlorinated sucrose-6-ester, particularly 4,1',6'-trichloro-4,1',6'-trideoxy-6-O-ester of galactosucrose (TGS-6E). Sucrose-6-ester can be prepared by esterification of sucrose. In accordance with any of the embodiments above, the chlorinating agent employed in the method is an acid chloride or an activated acid chloride. Examples of acid chlorides include thionyl chloride, sulfuryl chloride, phosgene, phosphorus pentachloride, oxalyl chloride, methane sulfonyl chloride, and bis(trichloromethyl)carbonate.

Examples of activated acid chloride include a Vilsmeier Reagent (also known as Arnold's reagent) having the formula: $[XYC=N^+R_2]Cl^-$, wherein X is hydrogen, aryl, or alkyl, wherein the aryl or alkyl is optionally substituted with a halogen, alkoxy, thioalkoxy, amido, or cyano; Y is a leaving group; and R is hydrogen or alkyl which is optionally substituted with halogen, alkoxy, thioalkoxy, amido, or cyano.

In accordance with an embodiment, in the formula of the Vilsmeier Reagent, Y is halogen, heteroalkyl, or a group capable of being displaced by a heteroatomic nucleophile, such as tosylate, brosylate, besylate, nosylate, mesylate, alkylfluorosulfonates, triflates, nonaflates, and tresylates, and in a particular example, halogen.

In accordance with an embodiment, in the formula of the Vilsmeier Reagent, X is hydrogen. In accordance with another embodiment, in the formula of the Vilsmeier Reagent, R and Y are alkyl. In accordance with yet another embodiment, in the formula of the Vilsmeier Reagent, X is hydrogen, Y is chloro, and R is methyl.

The Vilsmeier Reagent can be produced, for example, by the reaction of an acid chloride with an amide and used either as is or pre-reacted with a heteroatomic nucleophile YH to form an alternative comparably reactive reagent. Such a reagent can alternatively be formed prior to use in the chlorination reaction, or it may be formed in situ or it may be purchased from commercial sources. In an example, the Vilsmeier Reagent can be produced by the reaction of N,N-dimethylformamide with an acid chloride, for example, an acid chloride selected from the group consisting of thionyl chloride, sulfuryl chloride, phosgene, phosphorus pentachloride, oxalyl chloride, methane sulfonyl chloride, and bis(trichloromethyl)carbonate.

In accordance with any of the embodiments described above, the chlorination reaction can be carried out in a solvent system, for example, in a solvent system comprising one or more polar solvents, one or more non-polar solvents, or a mixture thereof. In an embodiment, the polar solvent is a polar aprotic solvent. Examples of the polar aprotic solvent include N,N-dimethylformamide, N,N-dimethylacetamide, N-methyl pyrrolidone, dimethylsulfoxide, sulfolane, and glycol ethers, and mixtures thereof.

In certain embodiments, the solvent system comprises a mixture of a polar aprotic solvent and at least one other aprotic solvent selected from the group consisting of chlorinated hydrocarbons and ethers. Examples of chlorinated hydrocarbons are chloroform, dichloromethane, dichloroethane, chlorofluorocarbons, dichloroethylene, trichloroethylene, trichloropropane, trichloroethane, dichloroethane, tetrachloroethane, and perfluorooctane, and mixtures thereof. In an embodiment, the ether is selected from the group consisting of tetrahydrofuran, dioxane, methoxyethane, dimethoxymethane, dimethoxyethane, tetrahydropyran, diglyme, diisopropyl ether, diethyl ether, and methyl t-butyl ether, and mixtures thereof. In a particular embodiment, the solvent system comprises N,N-dimethylformamide as the polar aprotic solvent.

For example, the carbohydrate-6-ester and the chlorinating agent are combined in the solvent at a suitable temperature, for example, between −30° C. and 25° C. During the addition of the chlorinating agent, the temperature is generally not allowed to rise above about 60° C., and in embodiments, above 50° C. Typically, the temperature is maintained from about 0° C. to about 30° C. Optionally, any HCl formed during the chlorination can be removed by any suitable method, e.g., by applying vacuum, by sonicating, by adsorbing on a suitable adsorbent such as carbon or zeolites, and/or by sparging an inert moisture free gas such as nitrogen, helium, air, or argon through the reaction mixture.

The chlorinating agent and the carbohydrate or derivative thereof to be chlorinated can be reacted in a suitable ratio, for example, in a ratio of 5 to 10 molar equivalents, preferably 7 to 8 molar equivalents of acid chloride.

In any of the above embodiments, the method can further include the step of (iv) quenching at least a portion of the reaction mixture obtained in step (i) to obtain a quenched reaction mixture. In accordance with the invention, the quenching step can be carried out by any suitable method, for example, by pouring the reaction mixture, preferably a cooled reaction mixture, e.g., at 5° C., into a cold basic solution such as aqueous alkali metal hydroxide, e.g., sodium or potassium hydroxide, an aqueous slurry of alkaline earth metal oxide or hydroxide, such as calcium oxide or hydroxide, aqueous ammonium hydroxide solution, or pyridine/methanol solution.

The quenched reaction mixture contains chlorinated carbohydrates or derivatives thereof, e.g., a mixture of the desired polychlorinated carbohydrate or derivative thereof and one or more of the under-chlorinated carbohydrates or derivatives thereof.

In accordance with an embodiment, the inventive method can further include the step of (v) isolating a product mixture comprising polychlorinated carbohydrate or derivative thereof and at least one under-chlorinated carbohydrate or derivative thereof from the quenched reaction mixture. The product mixture can be isolated by any suitable method known to those skilled in the art, for example, by solvent or solid phase extraction, chromatographic methods, crystallization, filtration, or any other method suitable for separating the desired mixture from the undesirable solvents and/or impurities.

In accordance with an embodiment of the method, the at least one under-chlorinated carbohydrate or derivative thereof is returned to a chlorination step, e.g., to step (i), to further chlorinate the under-chlorinated carbohydrate or derivative thereof. When the under-chlorinated carbohydrate or derivative thereof is returned to the chlorination step, the under-chlorinated carbohydrate or derivative thereof could be returned as a particular under-chlorinated carbohydrate or derivative thereof, as a mixture of under-chlorinated carbohydrates or derivatives thereof, or as a mixture the under-chlorinated carbohydrate or derivative thereof with other materials, for example, polychlorinated carbohydrate or derivative thereof.

In accordance with an embodiment of the method, the further chlorination of the at least one under-chlorinated carbohydrate or derivative thereof takes place in a vessel separate from the vessel where step (i) takes place.

In accordance with an embodiment of the method, the further chlorination of the at least one under-chlorinated carbohydrate or derivative thereof takes place in the same vessel where step (i) takes place.

In any of the embodiments, the method is a continuous feed method.

In any of the embodiments described above, the polychlorinated carbohydrate or derivative thereof, e.g., sucralose-6-ester, is obtained in step (i) in an yield of at least 30%, at least 40%, at least 50%, at least 60%, at least 70%, at least 80%, or at least 90%, on a molar basis and/or on a mass basis.

In any of the embodiments described above, the polychlorinated carbohydrate or derivative thereof, e.g., sucralose-6-ester, is obtained in step (iii) in an yield of at least 50%, at least 60%, at least 70%, at least 80%, or at least 90%, on a molar basis and/or on a mass basis.

In accordance with an embodiment of the method, the product mixture is isolated from the quenched reaction mixture by solvent extraction. The solvent used for the extraction is preferably a water immiscible solvent, for example, ethyl acetate, halocarbons, or any other solvent which forms a biphasic hydrophobic (organic) layer with a hydrophilic (aqueous) layer which enables partitioning and physical extractive separation of the desired product mixture from other impurities. This does not exclude incomplete partitioning, wherein some product remains partially dissolved in the aqueous layer requiring subsequent extractions. This also does not exclude incomplete partitioning, wherein some organic solvent is partially dissolved in the aqueous layer (e.g. DMF, DMA, ethyl acetate, etc.) nor the organic solvent partially dissolve in the aqueous layer (e.g. water, alcohols, etc.). The extract can be optionally decolorized to remove undesirable colored impurities. Decolorization can be carried out by any suitable method, for example, by treating with activated carbon.

In accordance with an embodiment of the invention, the method can further include the step of (vi) separating the product mixture isolated in step (v) into (a) a first fraction comprising the polychlorinated carbohydrate or derivative thereof and (b) a second fraction comprising at least one under-chlorinated carbohydrate or derivative thereof. The separation can be carried out by any suitable method, for example, solvent extraction taking advantage of the differing solubility properties of the polychlorinated carbohydrate or derivative thereof relative to the under-chlorinated carbohydrate or derivative thereof.

The first fraction can contain only the polychlorinated carbohydrate or derivative thereof or a mixture of the polychlorinated carbohydrate or derivative thereof and at least one under-chlorinated carbohydrate or derivative thereof; however, when it is a mixture of polychlorinated carbohydrate or derivative thereof and at least one under-chlorinated carbohydrate or derivative thereof, the first fraction contains an excess amount of the polychlorinated carbohydrate or derivative thereof relative to the under-chlorinated carbohydrate or derivative thereof.

The second fraction contains at least one under-chlorinated carbohydrate or derivative thereof. The second fraction can contain only one or more under-chlorinated carbohydrates or derivatives thereof, or it can contain a mixture of one or more under-chlorinated carbohydrates or derivatives thereof and polychlorinated carbohydrate or derivative thereof; however, when it is a mixture of under-chlorinated carbohydrate or derivative thereof and polychlorinated carbohydrate or derivative thereof, the second fraction contains an excess amount of the under-chlorinated carbohydrate or derivative thereof relative to the polychlorinated carbohydrate or derivative thereof.

In accordance with an embodiment of the invention, the polychlorinated carbohydrate or derivative thereof, the under-chlorinated carbohydrate or derivative thereof, or a mixture thereof, is optionally combined with additional carbohydrate or derivative thereof and returned to another chlorinating step, e.g., step (i) of the method, for further chlorination of the under-chlorinated carbohydrate or derivative thereof and optionally, chlorination of the additional carbohydrate or derivative thereof.

In a specific embodiment, the invention provides a method for chlorinating a carbohydrate or a derivative thereof to obtain a polychlorinated carbohydrate or derivative thereof, said polychlorinated carbohydrate or derivative thereof having a desired number of chlorine atoms in desired locations in its molecular structure, the method comprising:

(i) dissolving the carbohydrate or derivative thereof in an aprotic solvent system to obtain a solution comprising the carbohydrate or derivative thereof;

(ii) combining the solution comprising the carbohydrate or derivative thereof from step (i) with a chlorinating agent to obtain a chlorination mixture;

(iii) heating the chlorination mixture to obtain a mixture of chlorinated carbohydrates or derivatives thereof comprising the desired polychlorinated carbohydrate or derivative thereof and at least one under-chlorinated carbohydrate or derivative thereof having less than the desired number of chlorine atoms;

(iv) returning at least one under-chlorinated carbohydrate or derivative thereof to a chlorinating step so as to further chlorinate the at least one under-chlorinated carbohydrate or derivative thereof; and optionally (v) repeating steps (ii)-(iv) "n" times where n≥1.

The above method can further include a step of (vi) separating the polychlorinated carbohydrate or derivative thereof from the at least one under-chlorinated carbohydrates or derivatives thereof.

In accordance with an embodiment of the above method, the at least one under-chlorinated carbohydrate or derivative thereof is returned to step (i) for further chlorination.

In accordance with an embodiment of the above method, the further chlorination of the at least one under-chlorinated carbohydrate or derivative thereof takes place in a vessel separate from the vessel where step (i) takes place.

In accordance with an embodiment of the above method, the further chlorination of the at least one under-chlorinated carbohydrate or derivative thereof takes place in the same vessel where step (i) takes place.

In any of the embodiments, the above method is a continuous feed method.

In accordance with any of the embodiments above, the under-chlorinated carbohydrate or derivative thereof has one or two chlorine atoms in its molecular structure. In accordance with any of the embodiments above, the desired number of chlorine atoms present in the polychlorinated carbohydrate or derivative thereof is 3.

In any of the embodiments described above, the chlorination reaction followed by recovering and returning the under-chlorinated carbohydrate or derivative thereof can be repeated any number of times, and in a particular embodiment, to reach a steady state. In an embodiment, the recovering and returning can be performed for a "n" value in step (iii) or (v) of 2 to 8, 3 to 7, 4 to 6, or 5.

In any of the embodiments, in addition to recovering and returning the under-chlorinated carbohydrate or derivative thereof to the original chlorination step, additional non-chlorinated carbohydrate or derivative thereof, e.g., fresh sucrose-6-ester, can be combined with the returning under-chlorinated carbohydrate or derivative thereof.

In any of the embodiments described above, the sucralose-6-ester is obtained in step (i) in an yield of at least 30%, at least 40%, at least 50%, at least 60%, at least 70%, at least 80%, or at least 90%, on a molar basis and/or on a mass basis.

In any of the embodiments described above, the sucralose-6-ester is obtained in step (v) in an yield of at least 50%, at least 60%, at least 70%, at least 80%, or at least 90%, on a molar basis and/or on a mass basis.

The invention further provides a method of preparing sucralose comprising de-esterifying the polychlorinated sucrose 6-ester obtained in accordance with any of the embodiments above to obtain sucralose. For example, de-esterification can be carried out by alkaline hydrolysis of the ester; see, e.g., US '463, col. 9, lines 4-40 and Example 16, the disclosure of which is incorporated by reference.

The following example further illustrates the invention but, of course, should not be construed as in any way limiting its scope.

EXAMPLE

This example demonstrates a method of preparing sucralose in accordance with an embodiment of the invention. 0.05 mole sucrose-6-benzoate (S6B) (22.6 grams) was taken up in 850 mL of anhydrous N,N-dimethylformamide (DMF), pre-distilled under full vacuum to constant temperature (41° C., 75 mL distillate). The DMF solution was cooled to 5° C. (ice-bath) and 0.4 mole Vilsmeier (8 equivalents, 52 grams) was added. The resulting pale yellow suspension was stirred and warmed to ambient temperature over 30 min and then heated to 60° C. for 3 hours at which time, the suspension became a pale orange homogeneous solution. TLC analysis showed no more S6B was present. After cooling the solution, 600 mL of DMF-HCl (ca. 0.4 M) formed during the chlorination reaction was distilled off under full vacuum. The resulting reaction mixture was then heated to 87° C. for 8 hours. The reaction mixture was cooled to 5° C. and poured into 500 mL cold aqueous ammonium hydroxide. The resulting mixture was extracted with ethyl acetate (2×500 mL) to extract the 4,1',6'-trichloro-4,1',6'-trideoxy-6-O-benzoate ester of galactosucrose and any partially or under-chlorinated sucrose products. The extract was decolorized by stirring with activated carbon (10 g), and the extract was filtered through celite and concentrated under vacuum. The residue obtained was dissolved in ethyl acetate (100 mL) and washed with brine (2×50 mL) to remove the residual DMF. The resulting product was dried under vacuum for 30 min to remove further DMF and 19 grams of an amorphous foamy solid were obtained. The foamy solid was then dissolved in a mixture of methyl t-butyl ether (150 mL) and water (5 ml). TGS6B (13.9 g, 62% yield by mass, >95% purity) precipitated as an off-white solid upon vigorous stirring over 30 min and was collected by filtration. The filtrate (mother liquor) was concentrated to 8 grams.

The above procedure was repeated to scale on the 8 grams of mother liquor with the following exceptions: (175 mL DMF initial volume, 15 mL predistillation, 7 eq Vilsmeier, 20 g), and the reaction was held at 60° C. for only 30 min, and 125 mL of DMF was distilled off for the second distillation. This iteration provided another batch of TGS6B (4.1 g, 18% yield by mass, >95% pure) for a combined yield of 80% by mass. Another 3 grams of mother liquor containing ca. 1:1 mixture of di- and/or tri-chlorinated sucrose ester and and the same amount of the original higher $R_f$ material was also recovered. Each chlorination reaction was conducted for 8-10 hours at 87° C.

The yields obtained are as follows: $1^{st}$ iteration: 56% molar, 62% mass; $2^{nd}$ Iteration: 16.5% molar, 18% mass (based on original reaction); and the combined yield from the two iterations were: 72.5% molar, 80% mass. If the mother liquor was included, the combined yield was 84% molar, 93% mass.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention covers the following aspects:

1. A method for chlorinating a carbohydrate or a derivative thereof to produce a polychlorinated carbohydrate or a derivative thereof, said polychlorinated carbohydrate or a derivative thereof having a desired number of chlorine atoms in desired locations in its molecular structure, the method comprising:
    (i) reacting the carbohydrate or derivative thereof with a chlorinating agent to obtain a reaction mixture comprising said polychlorinated carbohydrate or derivative thereof and at least one under-chlorinated carbohydrate or derivative thereof;
    (ii) returning the at least one under-chlorinated carbohydrate or derivative thereof to a chlorinating step and further chlorinating the at least one under-chlorinated carbohydrate or derivative thereof to obtain the desired polychlorinated carbohydrate or derivative thereof; and
    (iii) optionally repeating steps (i) and (ii) "n" times where n≥1.
2. The method of aspect 1, further comprising:
    (iv) quenching at least a portion of the reaction mixture from step (i) to obtain a quenched reaction mixture and
    (v) isolating a product mixture comprising polychlorinated carbohydrate or derivative thereof and at least one under-chlorinated carbohydrate or derivative thereof from the quenched reaction mixture.
3. The method of aspect 1, wherein the at least one under-chlorinated carbohydrate or derivative thereof is returned to step (i) for further chlorination.
4. The method of aspect 1, wherein the further chlorination of the at least one under-chlorinated carbohydrate or derivative thereof takes place in a vessel separate from the vessel where step (i) takes place.
5. The method of aspect 1, wherein the further chlorination of the at least one under-chlorinated carbohydrate or derivative thereof takes place in the same vessel where step (i) takes place.
6. The method of any one of aspects 1 to 5, which is a continuous feed method.
7. The method of aspect 2, wherein in step (v), the product mixture is isolated from the quenched reaction mixture by solvent extraction.
8. The method of aspect 2 or 7, further comprising: (vi) separating the product mixture isolated in step (v) into (a) a first fraction comprising the polychlorinated carbohydrate or derivative thereof and (b) a second fraction comprising at least one under-chlorinated carbohydrate or derivative thereof.
9. The method of any one of aspects 1 to 8, wherein the polychlorinated carbohydrate or derivative thereof, under-chlorinated carbohydrate or derivative thereof, or a mixture thereof, is optionally combined with additional carbohydrate or derivative thereof and returned to a chlorinating step or to step (i).
10. The method of any one of aspects 1 to 9, wherein the carbohydrate or derivative thereof is a sugar or derivative thereof.
11. The method of aspect 10, wherein the sugar derivative is a sugar ester.
12. The method of aspect 11, wherein the sugar ester is a sucrose-6-ester.
13. The method of any one of aspects 1 to 12, wherein the polychlorinated carbohydrate derivative is 4,1',6'-trichloro-4,1',6'-trideoxy-6-O-ester of galactosucrose (TGS-6E).
14. The method of any one of aspects 11 to 13, wherein the polychlorinated carbohydrate ester or the under-chlorinated ester is of the formula:

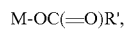

wherein R' comprises a hydrophobic group or a hydrophobic polymer and M is the moiety completing the rest of the polychlorinated carbohydrate ester or the under-chlorinated ester.
15. The method of aspect 14, wherein R' comprises a hydrophobic group or a hydrophobic polymer such that the polychlorinated carbohydrate ester or the under-chlorinated ester has an octanol-water partition coefficient cLogP of −0.5 or greater.
16. The method of aspect 14, wherein the polychlorinated carbohydrate ester or the under-chlorinated carbohydrate ester has an octanol-water partition coefficient cLogP of 0 or greater than 0.
17. The method of aspect 14, wherein R is alkyl, aryl, or arylalkyl, wherein the aryl part of aryl or arylalkyl is optionally substituted with one or more substituents selected from the group consisting of halo, haloalkyl, cyano, nitro, alkoxy, alkylthio, acyl, acyloxy, thioacyl, acylthio, and aryloxy.
18. The method of aspect 14, wherein R' is aryl.
19. The method of aspect 18, wherein R' is phenyl.
20. The method of aspect 14, wherein R' comprises a hydrophobic polymer.
21. The method of any one of aspects 1 to 20, wherein the chlorinating agent is an acid chloride or an activated acid chloride.
22. The method of aspect 21, wherein the acid chloride is selected from the group consisting of thionyl chloride, sulfuryl chloride, phosgene, phosphorus pentachloride, oxalyl chloride, methane sulfonyl chloride, and bis(trichloromethyl) carbonate.
23. The method of aspect 21, wherein the activated acid chloride is a Vilsmeier Reagent [or Arnold's reagent] having the formula: $[XYC=N^+R_2]Cl^-$, wherein X is hydrogen, aryl, or alkyl, wherein the aryl or alkyl is optionally substituted with a halogen, alkoxy, thioalkoxy, amido, or cyano; Y is a leaving group; and R is hydrogen or alkyl which is optionally substituted with halogen, alkoxy, thioalkoxy, amido, or cyano.
24. The method of aspect 23, wherein Y is halogen, heteroalkyl, or a group capable of being displaced by a heteroatomic nucleophile.
25. The method of aspect 24, wherein Y is halogen.
26. The method of aspect 23, wherein X is hydrogen.
27. The method of aspect 23, wherein R and Y are alkyl.
28. The method of any one of aspects 23 to 26, wherein X is hydrogen, Y is chloro, and R is methyl.

29. The method of aspect 28, wherein the Vilsmeier Reagent is produced by the reaction of N,N-dimethylformamide with an acid chloride.

30. The method of aspect 29, wherein the acid chloride is selected from the group consisting of thionyl chloride, sulfuryl chloride, phosgene, phosphorus pentachloride, oxalyl chloride, methane sulfonyl chloride, and bis(trichloromethyl) carbonate.

31. The method of any one of aspects 1 to 30, wherein the chlorination reaction is carried out in a solvent system.

32. The method of aspect 31, wherein the solvent system comprises one or more polar solvents, one or more non-polar solvents, or a mixture thereof.

33. The method of aspect 32, wherein the polar solvent is a polar aprotic solvent.

34. The method of aspect 33, wherein the polar aprotic solvent is selected from the group consisting of N,N-dimethylformamide, N,N-dimethylacetamide, N-methyl pyrrolidone, dimethylsulfoxide, sulfolane, and glycol ethers.

35. The method of aspect 31, wherein the solvent system comprises a mixture of a polar aprotic solvent and at least one other aprotic solvent selected from the group consisting of chlorinated hydrocarbons and ethers.

36. The method of aspect 35, wherein the chlorinated hydrocarbon is selected from the group consisting of chloroform, dichloromethane, dichloroethane, chlorofluorocarbons, dichloroethylene, trichloroethylene, trichloropropane, trichloroethane, dichloroethane, tetrachloroethane, and perfluorooctane.

37. The method of aspect 35, wherein the ether is selected from the group consisting of tetrahydrofuran, dioxane, methoxyethane, dimethoxymethane, dimethoxyethane, tetrahydropyran, diglyme, diisopropyl ether, diethyl ether, and methyl t-butyl ether.

38. The method of any one of aspects 32 to 37, wherein the solvent system comprises N,N-dimethylformamide as the polar aprotic solvent.

39. A method for chlorinating a carbohydrate or a derivative thereof to obtain a polychlorinated carbohydrate or derivative thereof, said polychlorinated carbohydrate or derivative thereof having a desired number of chlorine atoms in desired locations in its molecular structure, the method comprising:
(i) dissolving the carbohydrate or derivative thereof in an aprotic solvent system to obtain a solution comprising the carbohydrate or derivative thereof;
(ii) combining the solution comprising the carbohydrate or derivative thereof from step (i) with a chlorinating agent to obtain a chlorination mixture;
(iii) heating the chlorination mixture to obtain a mixture of chlorinated carbohydrates or derivatives thereof comprising the desired polychlorinated carbohydrate or derivative thereof and at least one under-chlorinated carbohydrate or derivative thereof having less than the desired number of chlorine atoms;
(iv) returning at least one under-chlorinated carbohydrate or derivative thereof to a chlorinating step so as to further chlorinate the at least one under-chlorinated carbohydrate or derivative thereof; and optionally
(v) repeating steps (ii)-(iv) "n" times where n≥1.

40. The method of aspect 39, further comprising (vi) separating the polychlorinated carbohydrate or derivative thereof from the at least one under-chlorinated carbohydrates or derivatives thereof.

41. The method of aspect 39, wherein the at least one under-chlorinated carbohydrate or derivative thereof is returned to step (i) for further chlorination.

42. The method of aspect 39, wherein the further chlorination of the at least one under-chlorinated carbohydrate or derivative thereof takes place in a vessel separate from the vessel where step (i) takes place.

43. The method of aspect 39, wherein the further chlorination of the at least one under-chlorinated carbohydrate or derivative thereof takes place in the same vessel where step (i) takes place.

44. The method of any one of aspects 39 to 43, which is a continuous feed method.

45. The method of any one of aspects 1 to 44, wherein the polychlorinated carbohydrate or derivative thereof is a polychlorinated sucrose-6-ester.

46. The method of aspect 45, wherein the polychlorinated carbohydrate is sucralose-6-ester.

47. The method of aspect 46, wherein the sucralose-6-ester is obtained in step (i) in an yield of at least 30%.

48. The method of aspect 47, wherein the sucralose-6-ester is obtained in step (i) in an yield of at least 40%.

49. The method of aspect 48, wherein the sucralose-6-ester is obtained in step (i) in an yield of at least 50%.

50. The method of aspect 39, wherein the sucralose-6-ester is obtained in step (v) in an yield of at least 50%.

51. The method of aspect 50, wherein sucralose-6-ester is obtained in step (v) an yield of the yield of at least 60%.

52. The method of aspect 51, wherein the sucralose-6-ester is obtained in step (v) in an yield of at least 70%.

53. The method of aspect 52, wherein sucralose-6-ester is obtained in step (v) an yield of the yield of at least 80%.

54. The method of aspect 53, wherein sucralose-6-ester is obtained in step (v) an yield of the yield of at least 90%.

55. The method of aspect 1, wherein the polychlorinated carbohydrate or derivative thereof is obtained in step (i) in an yield of at least 30%.

56. The method of aspect 55, wherein the polychlorinated carbohydrate or derivative thereof is obtained in step (i) in an yield of at least 40%.

57. The method of aspect 56, wherein the polychlorinated carbohydrate or derivative thereof is obtained in step (i) in an yield of at least 50%.

58. The method of aspect 1, wherein the polychlorinated carbohydrate or derivative thereof is obtained in step (iii) in an yield of at least 50%.

59. The method of aspect 58, wherein polychlorinated carbohydrate or derivative thereof is obtained in step (iii) in an yield of the yield of at least 60%.

60. The method of aspect 59, wherein the polychlorinated carbohydrate or derivative thereof is obtained in step (iii) in an yield of at least 70%.

61. The method of aspect 60, wherein polychlorinated carbohydrate or derivative thereof is obtained in step (iii) in an yield of the yield of at least 80%.

62. The method of aspect 61, wherein polychlorinated carbohydrate or derivative thereof is obtained in step (iii) in an yield of the yield of at least 90%.

63. A method of preparing sucralose comprising de-esterifying the polychlorinated sucrose 6-ester obtained according to any one of aspects 1 to 62 to obtain sucralose.

64. The method of any one of aspects 1 to 62, wherein the under-chlorinated carbohydrate or derivative thereof has one or two chlorine atoms in its molecular structure.

65. The method of aspect 1 or 39, wherein the desired number of chlorine atoms present in the polychlorinated carbohydrate or derivative thereof is 3.

The invention claimed is:
1. A method for chlorinating a sucrose-6-ester to produce 4,1',6'-trichloro-4,1',6'-trideoxy-6-O-ester of galactosucrose

(TGS-6E) of the formula M-OC(=O)R', wherein R' is a hydrophobic group such that TGS-6E has an octanol-water partition coefficient cLogP of 0.5 or greater, and M is the moiety completing the rest of TGS-6E, the method comprising:
  (i) reacting the sucrose-6-ester with a chlorinating agent in N,N-dimethylformamide (DMF) to obtain a chlorination reaction mixture, and removing at least a portion of the HCl resulting from the chlorination reaction as a DMF-HCl mixture by vacuum distillation, to obtain a reaction mixture comprising said TGS-6E and at least one under-chlorinated sucrose-6-ester of the formula M'-OC(=O)R', wherein R' is a hydrophobic group such that the under-chlorinated sucrose-6-ester has an octanol-water partition coefficient cLogP of 0.5 or greater, and M' is the moiety completing the rest of the under-chlorinated sucrose-6-ester;
  (ii) returning the at least one under-chlorinated sucrose-6-ester to a chlorinating step and further chlorinating the at least one sucrose-6-ester to obtain TGS-6E; and
  (iii) optionally repeating steps (i) and (ii) "n" times where $n \geq 1$.

2. The method of claim 1, further comprising:
  (iv) quenching at least a portion of the reaction mixture from step (i) to obtain a quenched reaction mixture and
  (v) isolating a product mixture comprising TGS-6E and at least one under-chlorinated sucrose-6-ester from the quenched reaction mixture.

3. The method of claim 1, wherein the at least one under-chlorinated sucrose-6-ester is returned to step (i) for further chlorination.

4. The method of claim 1, wherein the further chlorination of the at least one under-chlorinated sucrose-6-ester takes place in a vessel separate from the vessel where step (i) takes place.

5. The method of claim 1, wherein the further chlorination of the at least one under-chlorinated sucrose-6-ester takes place in the same vessel where step (i) takes place.

6. The method of claim 2, wherein in step (v), the product mixture is isolated from the quenched reaction mixture by solvent extraction.

7. The method of claim 2, further comprising: (vi) separating the product mixture isolated in step (v) into (a) a first fraction comprising TGS-6E and (b) a second fraction comprising at least one under-chlorinated sucrose-6-ester.

8. The method of claim 1, wherein TGS-6E, the at least one under-chlorinated sucrose-6-ester, or a mixture thereof, is optionally combined with additional sucrose-6-ester and returned to a chlorinating step or to step (i).

9. The method of claim 1, wherein R' is phenyl.

10. The method of claim 1, wherein the chlorinating agent is an acid chloride, an activated acid chloride, or bis(trichloromethyl)carbonate.

11. The method of claim 10, wherein the acid chloride is selected from the group consisting of thionyl chloride, sulfuryl chloride, phosgene, phosphorus pentachloride, oxalyl chloride, and methanesulfonyl chloride.

12. The method of claim 10, wherein the activated acid chloride is a Vilsmeier Reagent having the formula: $[XYC=N^+R_2]Cl^-$, wherein X is hydrogen, aryl, or alkyl, wherein the aryl or alkyl is optionally substituted with a halogen, alkoxy, thioalkoxy, amido, or cyano; Y is a leaving group; and R is hydrogen or alkyl which is optionally substituted with halogen, alkoxy, thioalkoxy, amido, or cyano.

13. The method of claim 12, wherein Y is halogen, heteroalkyl, or a group capable of being displaced by a heteroatomic nucleophile.

14. The method of claim 12, wherein X is hydrogen, Y is chloro, and R is methyl.

15. A method for chlorinating sucrose-6-benzoate ester to produce 4,1',6'-trichloro-4,1',6'-trideoxy-6-O-benzoate ester of galactosucrose (TGS-6B), the method comprising:
  (a) dissolving the sucrose-6-benzoate ester in N,N-dimethylformamide (DMF) to obtain a solution comprising the sucrose-6-benzoate ester;
  (b) combining the solution comprising the sucrose-6-benzoate ester from step (i) with a chlorinating agent to obtain a chlorination mixture;
  (c) removing by vacuum distillation at least a portion of the HCl resulting from the chlorination reaction as a DMF-HCl mixture to obtain a reaction mixture comprising TGS-6B and at least one-under chlorinated sucrose-6-benzoate ester;
  (d) returning the at least one under-chlorinated sucrose-6-benzoate ester to a chlorinating step so as to further chlorinate the at least one under-chlorinated sucrose-6-benzoate ester; and optionally
  (e) repeating steps (b)-(d) "n" times where $n \geq 1$.

16. The method of claim 15, further comprising (f) separating the TGS-6B from the at least one under-chlorinated sucrose-6-benzoate ester.

17. The method of claim 15, wherein the at least one under-chlorinated sucrose-6-benzoate ester is returned to step (a) for further chlorination.

18. A method of preparing sucralose comprising de-esterifying the TGS-6B obtained according to claim 15 to obtain sucralose.

19. The method of claim 1, wherein n=2 to 8.

20. The method of claim 1, wherein the at least one under-chlorinated sucrose-6-ester is dichlorogalactosucrose-6-benzoate.

21. The method of claim 1, wherein the at least one under-chlorinated sucrose-6-ester is monochlorogalactosucrose-6-benzoate.

22. The method of claim 15, wherein n=2 to 8.

23. The method of claim 15, wherein the at least one under-chlorinated sucrose-6-ester is dichlorogalactosucrose-6-benzoate.

24. The method of claim 15, wherein the at least one under-chlorinated sucrose-6-ester is monochlorogalactosucrose-6-benzoate.

* * * * *